(12) United States Patent
Sabel et al.

(10) Patent No.: US 8,756,190 B2
(45) Date of Patent: Jun. 17, 2014

(54) APPARATUS AND A METHOD FOR AUTOMATIC TREATMENT ADJUSTMENT AFTER NERVOUS SYSTEM DYSFUNCTION

(75) Inventors: Bernhard A. Sabel, Berlin (DE); Tobias Günther, Magdeburg (DE); Iris Müller, Vechelde (DE)

(73) Assignee: EBS Technologies GmbH, Kleinmachnow (DE)

( * ) Notice: Subject to any disclaimer, the term of this patent is extended or adjusted under 35 U.S.C. 154(b) by 370 days.

(21) Appl. No.: 12/933,573

(22) PCT Filed: Mar. 20, 2008

(86) PCT No.: PCT/EP2008/053416
§ 371 (c)(1),
(2), (4) Date: Nov. 30, 2010

(87) PCT Pub. No.: WO2009/115129
PCT Pub. Date: Sep. 24, 2009

(65) Prior Publication Data
US 2011/0066586 A1    Mar. 17, 2011

(51) Int. Cl.
*G06N 7/06* (2006.01)

(52) U.S. Cl.
USPC .......................................................... 706/52

(58) Field of Classification Search
None
See application file for complete search history.

(56) References Cited

U.S. PATENT DOCUMENTS

| | | | |
|---|---|---|---|
| 4,626,090 A * | 12/1986 | Charlier et al. | 351/226 |
| 4,979,508 A * | 12/1990 | Beck | 607/54 |
| 6,066,163 A * | 5/2000 | John | 607/45 |
| 6,199,018 B1 * | 3/2001 | Quist et al. | 702/34 |
| 6,729,728 B2 * | 5/2004 | Wei et al. | 351/211 |
| 6,834,237 B2 * | 12/2004 | Noergaard et al. | 702/19 |
| 6,990,377 B2 * | 1/2006 | Gliner et al. | 607/54 |
| 7,027,874 B1 * | 4/2006 | Sawan et al. | 607/116 |
| 7,120,614 B2 * | 10/2006 | Ikeda et al. | 706/14 |
| 7,483,747 B2 * | 1/2009 | Gliner et al. | 607/45 |
| 7,606,405 B2 * | 10/2009 | Sawyer et al. | 382/128 |
| 7,610,096 B2 * | 10/2009 | McDonald, III | 607/48 |
| 7,769,441 B2 * | 8/2010 | Foreman et al. | 607/2 |
| 7,983,762 B2 * | 7/2011 | Gliner et al. | 607/115 |
| 7,991,477 B2 * | 8/2011 | McDonald, III | 607/48 |

(Continued)

FOREIGN PATENT DOCUMENTS

| | | | |
|---|---|---|---|
| EP | 1 378 851 | 1/2004 | G06F 19/00 |
| WO | WO 00/12042 | 3/2000 | A61H 5/00 |
| WO | WO 03/082162 | 10/2003 | A61F 9/00 |

OTHER PUBLICATIONS

Guenther et al., "Data INfrastructure of Prediction Models for the Diagnosis and Treatment Outcome in Patients with Visual System Dysfunction," International Conference Computational Intelligence in Medicine and Healthcare, Jul. 25, 2007, 7pp, XP009110368.*

(Continued)

*Primary Examiner* — Kakali Chaki
*Assistant Examiner* — Fuming Wu
(74) *Attorney, Agent, or Firm* — Gerald T. Bodner (57) ABSTRACT

The present invention relates to an apparatus for automatic adjustment of a treatment of a target person to be treated based on calculated recovery prediction data for predicting a change of a sensory function of said target person in response to said treatment.

2 Claims, 9 Drawing Sheets

(56) References Cited

U.S. PATENT DOCUMENTS

| | | | |
|---|---|---|---|
| 2003/0100924 A1* | 5/2003 | Foreman et al. | 607/9 |
| 2003/0158828 A1* | 8/2003 | Ikeda et al. | 706/12 |
| 2004/0023197 A1 | 2/2004 | Abraham-Fuchs et al. | 434/236 |
| 2004/0156554 A1* | 8/2004 | McIntyre | 382/254 |
| 2004/0193019 A1* | 9/2004 | Wei | 600/300 |
| 2006/0106432 A1* | 5/2006 | Sawan et al. | 607/54 |
| 2006/0134671 A1* | 6/2006 | Burczynski et al. | 435/6 |
| 2006/0194211 A1* | 8/2006 | Burczynski et al. | 435/6 |
| 2007/0014454 A1* | 1/2007 | Sawyer et al. | 382/128 |
| 2007/0191895 A1* | 8/2007 | Foreman et al. | 607/14 |
| 2007/0260285 A1* | 11/2007 | Libbus et al. | 607/9 |
| 2008/0032299 A1* | 2/2008 | Burczynski et al. | 435/6 |
| 2008/0103409 A1* | 5/2008 | Komissarov | 600/558 |
| 2008/0114219 A1* | 5/2008 | Zhang et al. | 600/301 |
| 2008/0188763 A1* | 8/2008 | John et al. | 600/516 |
| 2008/0226645 A1* | 9/2008 | O'Toole et al. | 424/139.1 |
| 2009/0081296 A1* | 3/2009 | Humes et al. | 424/488 |
| 2009/0312817 A1* | 12/2009 | Hogle et al. | 607/54 |
| 2010/0249532 A1* | 9/2010 | Maddess et al. | 600/300 |

OTHER PUBLICATIONS

Each of the International Preliminary Report on Patentability, in English, dated Sep. 21, 2010, the Written Opinion of the International Searching Authority, in English, dated Sep. 20, 2010 and the International Search Report, in English, dated Feb. 25, 2009, issued from Applicants' corresponding PCT Application No. PCT/EP2008/053416, filed Mar. 20, 2008, each from the World Intellectual Property Organization (WIPO) is enclosed.

Günther T., et al.: "*Data Infrastructure of Prediction Models for the Diagnosis and Treatment Outcome in Patients with Visual System Dysfunction*", International Conference Computational Intelligence in Medicine and Healthcare, vol. $3^{rd}$ conference (Jul. 25, 2007), p. 7pp, XP009110368. Conference information accessible at: http://www.allconferences.com/conferences/2006/20061130152436 Text available at: http://scholar.googleusercontent.com/scholar?q=cache:mP8YgkTZF4J:scholar.google.com (accessed: Oct. 25, 2013).

Chang, Chih-Chung and Chih-Jen Lin, "*LIBSVM: A Library for Support Vector Machines*", ACM Transactions on Intelligent Systems and Technology, 2:27:1—27:27 (2011), Program information available at http://www.csie.ntu.edu.tw/~cjlin/libsvm/, Text available at: http://www.csie.ntu.edu.tw/~cjlin/papers/libsym (accessed: Oct. 25, 2013).

Nürnberger, Andreas, Witold Pedrycz and Rudolf Kruse, "Data Mining Tasks and Methods: Classification: Neural Network Approaches",*Handbook of Data Mining and Knowledge Discovery*, Willi Klösgen and Jan M. Zytkow, ed. New York: Oxford University Press (2002) pp. 304-317 Print ISBN: 0-19-511831-6. Book Information available at: http://dl.acm.org/citation.cfm?id=778212 and http://www.amazon.com/Handbook-Data-Mining-Knowledge-Discovery/dp/ 0195118316.

Quinlan, J. Ross, "*C4.5: Programs for Machine Learning*", San Francisco, CA: Morgan Kaufmann Publishers (1993) Print ISBN 1-55860-238-0. Book information available at: http://www.amazon.com/C4-5Programs-Machine-Learning-Kaufmann/dp/1558602380, Text available at http://www.tnove.com/wp-content/uploads/2013/01/c4.5.pdf 312 pages.

Tan, Pang-Ning, Michael Steinback and Vipin Kumar, "*Introduction to Data Mining*", Boston MA: Addison-Wesley (Mar. 25, 2006) 169 pages ISBN-10: users.cs.umm.edu/~kumar/dmbook/index.php.

\* cited by examiner

APPARATUS AND A METHOD FOR AUTOMATIC TREATMENT ADJUSTMENT AFTER NERVOUS SYSTEM DYSFUNCTION

CROSS REFERENCE TO RELATED APPLICATIONS

This application is a U.S. National Stage Application of International Patent Application No. PCT/EP2008/053416, filed Mar. 20, 2008.

The invention relates to a method and an apparatus for automatic adjustment of a treatment using a treatment outcome prediction model.

Brain injuries caused by stroke, trauma or tumour can affect the sensory function of a person. The sensory organ affected by disease can be a visual organ, an auditory organ or a touch organ of a person. To recover sensory functions of the affected person, the person can be treated, for example by stimulation of the affected sensory organ, such as the eye of the person. Other treatments, such as the application of drugs or electrical stimulation are also possible. Each treatment comprises treatment parameters which can be adjusted for the respective target person. When the affected sensory organ is a visual organ of a person or a patient, it is possible to perform a visual stimulation training VST of the damaged visual field and its border region. A stimulation device, e.g. a display supplies a stimulation signal to the affected sensory organ. Treatment parameters, such as the intensity and frequency of the applied stimulation signal can be adjusted.

Since each patient or person has an individual sensory defect, it is necessary to optimize the settings of the treatment parameters to achieve good treatment results. With conventional treatment apparatuses, the treatment of sensory organs of an affected person is performed without taking into account sensory data of the target person and a priori knowledge, i.e. the sensory data of a reference group of persons already treated with said treatment. A conventional treatment apparatus which treats a sensory organ by applying a stimulation signal to the target person does not adjust the parameters of the stimulation signal according to the recorded reaction of the target person. Each person having deficits of its sensory organ is treated in the same manner as other patients or persons. For example, each person having a damaged visual field is treated with the same sequence of visual stimulation signals during a treatment session without considering sensory data measured automatically, for example by means of electrodes or taking into account feedback given by the person to the physician. Accordingly, with a conventional apparatus, the treatment parameters of the treatment are not optimized to the individual sensory function defect of the target person. Furthermore, with a conventional treatment apparatus it is not possible to predict the treatment outcome for an individual target person.

Accordingly, it is an object of the present invention to provide an apparatus and a method for predicting a treatment outcome and for optimizing a treatment for a target person.

This object is achieved by an apparatus having the features of claim 1.

The invention provides an apparatus for automatic adjustment of a treatment for a target person to be treated based on calculated recovery prediction data predicting a change of a sensory function of said target person in response to said treatment.

In an embodiment of the apparatus according to the present invention, the recovery prediction data is calculated by data mining on the basis of sensory data of the target person and on the basis of sensory data of a reference group of persons treated by said treatment.

In an embodiment of the apparatus according to the present invention, the apparatus comprises a processing unit for executing a data mining algorithm to calculate the recovery prediction data.

In an embodiment of the apparatus according to the present invention, the data mining algorithm is a classification algorithm, such as Self-Organizing Map (SOM), linear regression algorithms, Support-Vector-Machines, Neural Networks, k-Nearest-Neighbor, Decision Trees etc.

In an embodiment of the apparatus according to the present invention, the apparatus comprises a storage device for storing the sensory data of the target person and the sensory data of the reference group.

In an embodiment of the apparatus according to the present invention, the apparatus comprises at least one detection device for measuring sensory data of said target person.

In an embodiment of the apparatus according to the present invention, the sensory data comprises recorded data detected for a sensory organ or associated brain regions of said sensory organ.

In an embodiment of the apparatus according to the present invention, the sensory organ comprises a visual organ, an acoustical organ or a touch organ of said target person.

In an embodiment of the apparatus according to the present invention, the treatment is a stimulation treatment of said sensory organ.

In an embodiment of the apparatus according to the present invention, the stimulation treatment of said sensory organ comprises a functional stimulation and/or an electrical stimulation of said sensory organ.

In an embodiment of the apparatus according to the present invention, the electrical stimulation of said sensory organ comprises an invasive or a non-invasive electrical stimulation of said sensory organ.

In an embodiment of the apparatus according to the present invention, at least one parameter of said stimulation treatment is adjusted depending on said recovery prediction data calculated by said processing unit.

In an embodiment of the apparatus according to the present invention, the sensory data comprises global feature data and local feature data.

In an embodiment of the apparatus according to the present invention, the global feature data comprises a size of a residual area and a size of a defect area of a sensory organ of said target person.

In an embodiment of the apparatus according to the present invention, the global feature data further comprises a reaction time of said target person to a stimulation signal.

In an embodiment of the apparatus according to the present invention, the global feature data comprises conformity data of a visual field chart of said target person indicating a degree of similarity of the visual field to heminopia and quadrantanopia.

In an embodiment of the apparatus according to the present invention, the global feature data comprises order diffuseness data indicating an extent to which a visual field border of said target person in diffused.

In an embodiment of the apparatus according to the present invention, the local feature data comprises neighborhood data of a spot in a visual field chart of said target person.

In an embodiment of the apparatus according to the present invention, the local feature data comprises distance data indicating a distance of a spot to a visual field defect border in a visual field chart of said target person.

In an embodiment of the apparatus according to the present invention, the local feature data comprises a visual field position of a spot in a visual field chart of said target person.

In an embodiment of the apparatus according to the present invention, the local feature data comprises a residual function value of a spot in a visual field chart of said target person.

The invention further provides a method for automatic adjustment of treatment for a target person to be treated based on recovery prediction data predicting a change of a sensory function of the target person in response to said treatment.

In an embodiment of the method according to the present invention, the recovery prediction data is calculated by data mining on the basis of sensory data of the target person and on the basis of sensory data of a reference group treated by said treatment.

The invention further provides a computer program comprising instructions for executing a method for automatic adjustment of a treatment for a target person to be treated based on recovery prediction data predicting a change of a sensory function of said target person in response to said treatment.

The invention further provides a data carrier for storing a computer program comprising instructions for executing a method for automatic adjustment of a treatment for a target person to be treated based on recovery prediction data predicting a change of a sensory function of the target person in response to said treatment.

In the following, preferred embodiments of the apparatus and method according to the present invention are described with reference to the enclosed figures.

Figure 1:
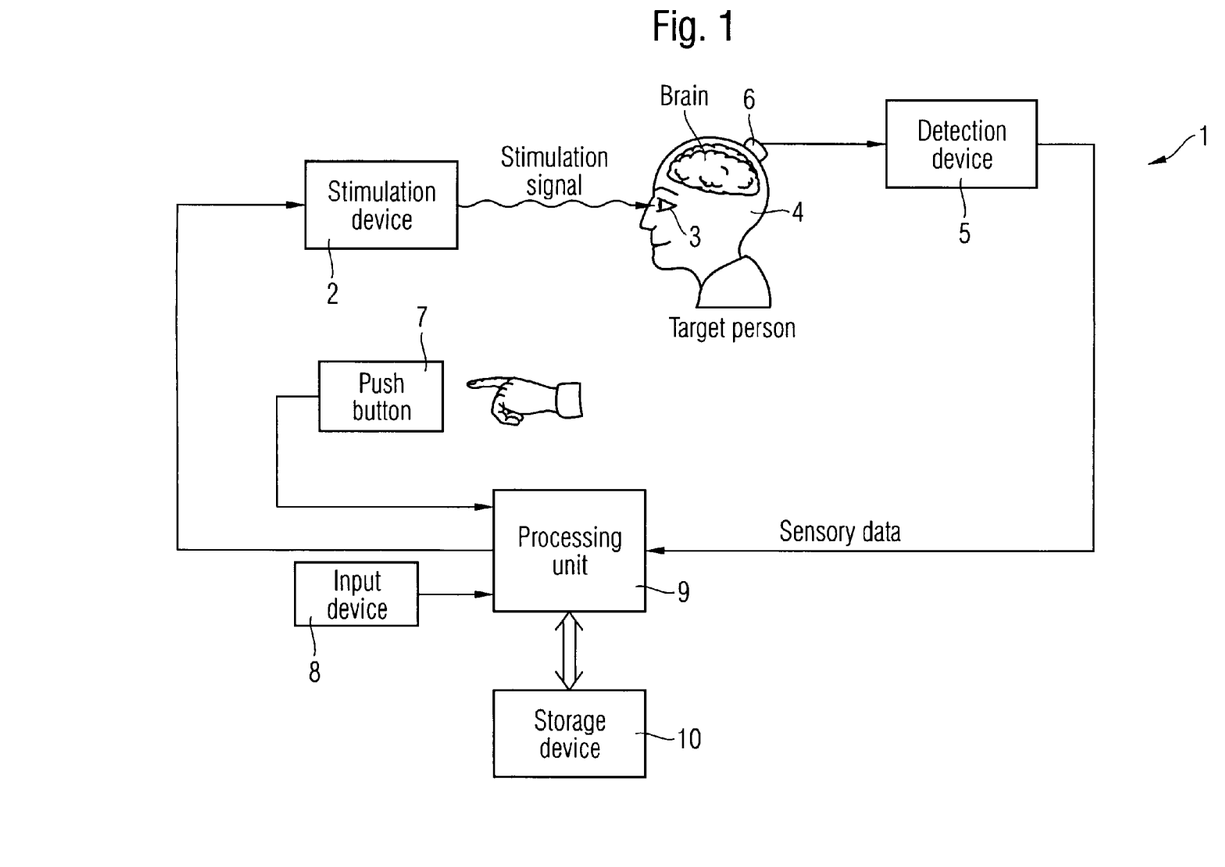
FIG. 1 shows a block diagram of a possible embodiment of an apparatus for automatic adjustment of a treatment of a target person according to the present invention.

As can be seen from FIG. 1, in a possible embodiment the apparatus 1 for automatic adjustment of a treatment according to the present invention comprises a stimulation device 2 for generating a stimulation signal applied to a sensory organ 3 of a target person 4. In the example as shown in FIG. 1, the sensory organ 3 of the target person 4 is formed by a visual organ of the target person 4, i.e. an eye of the target person. In the embodiment as shown in FIG. 1, the apparatus 1 further comprises at least one detection device 5 for measuring sensory data of said target person 4. In a possible embodiment, the detection device 5 is connected to a electrode 6 attached to the head of the target person 4. In the embodiment as shown in FIG. 1, the detection device 5 measures sensory data of the target person 4 detected for a sensory organ 3 associated brain regions of the sensory organ.

In a possible embodiment, the target person 4 further can give a feedback by pressing a push-button 7 in response to the applied stimulation signal. In a further embodiment, the target person 4 can give a feedback by talking to a physician which inputs the feedback via an input device, such as a keyboard 8. The sensory data measured by the detection device 5 as well as the feedback data of the target person 4 are applied to a processing unit 9 of the apparatus 1. The processing unit 9 is connected to the detection device 5, the push-button 7 and the input device 8. Furthermore, the processing unit 9 controls via control lines the stimulation device 2. In a possible embodiment, the stimulation device 2 is formed by a display. The processing unit 9 is connected also to a storage device 10. The storage device 10 stores sensory data of said target person 4 and sensory data of a reference group of other persons already treated with the stimulation signal. The processing unit 9 can be formed by a micro-processor executing a computer program for automatic adjustment of the treatment of the target person 4. In the embodiment as shown in FIG. 1, the processing unit 9 controls treatment parameters of the stimulation signal generated by the stimulation device 2. Such treatment parameters can be, for example the intensity and the frequency of the stimulation signal applied to the visual organ 3 of the target person 4. The applied treatment is adjusted automatically by the processing unit 9 based on calculated recovery prediction data. The processing unit 9 calculates the recovery prediction data predicting a change of a sensory function of the target person 4 in response to a treatment applied to the target person 4. This recovery prediction data is calculated in an embodiment by data mining on the basis of sensory data of the target person 4 stored in the storage device 10 and on the basis of sensory data of a reference group of persons already treated by the treatment. The processing unit 9 executes a data mining algorithm to calculate the recovery prediction data. In a possible embodiment, the data mining algorithm is formed by a self-organizing map (SOM)-algorithm. In further embodiments, the data mining algorithm is formed by other classification algorithms, such as linear regression algorithms, support vector machines, neural networks, K-nearest-neighbor and decision on trees as described for instance in P. N. Tan, M. Steinbach, and V. Kumar. Introduction to data mining. Pearson Addison-Wesley, 2006; C.-C. Chang and C.-J. Lin, "LIBSVM: a library for support vector machines", Software available at http://www.csie.ntu.edu.tw/~cjlin/libsvm, 2001; J. R. Quinlan, C4.5: programs for machine learning, Morgan Kaufmann Publishers Inc., San Francisco, Calif., USA, 1993, ISBN 1-55860-238-0; A. Nuernberger, W. Pedrycz, and R. Kruse, Neural network approaches, pages 304-317, 2002.

In the embodiment as shown in FIG. 1, the stimulation signal is a visual stimulation signal which performs a functional simulation of the sensory organ 3. In a possible embodiment, the affected sensory organ 3 of the target person is simultaneously stimulated by an electrical signal. In a further embodiment, the target person 4 is stimulated only by electrical stimulation signals. The electrical simulation signals can be applied to the head of the target person 4 by means of stimulation electrodes. In a possible embodiment, the electrical stimulation of the sensory organ 3 is performed by a non-invasive electrical stimulation of the sensory organ. In an alternative embodiment, the electrical stimulation can be performed by an invasive electrical stimulation of the sensory organ 3. At least one parameter of the electrical or functional stimulation treatment of the target person 4 is adjusted depending on the recovery prediction data calculated by the processing unit 9.

The sensory data measured by the detection device 5 and stored temporarily in the storage device 10 as well as the sensory data of other patients or persons of a reference group already treated comprise global feature data and local feature data. The global feature data and the local feature data of the target person 4 as well as of the persons in the reference group are stored in the storage device 10. The global feature data comprises a size of a residual area and a size of a defect area of a sensory organ 3 of the target person 4. In a possible embodiment, global feature data 4 further comprises a reaction time of said target person 4 to a stimulation signal as applied to the sensory organ 3 of the target person 4. The reaction time can be measured as the time delay which the target person 4 needs to press the push-button 7 in reaction to a stimulation signal. The global feature data can comprise conformity data of a visual field of the target person 4 indicating a degree of similarity of the visual field to heminopia and quadrantanopia. The global feature data further comprises in a possible embodiment border diffuseness data indicating an extent to which the visual field border of said target person 4 is diffused.

Besides the global feature data the sensory data stored in the storage device 10 comprises local feature data. Local feature data relates to a specific spot in a visual field chart of the target person 4. In a possible embodiment of the apparatus according to the present invention as shown in FIG. 1, the local feature data comprises neighborhood data of a spot in a visual field chart of the target person 4. The neighborhood data comprises for instance the neighborhood activity around the respective spot in the visual field chart. The neighborhood data can comprise the variability of the residual activity in the immediate surrounding of the respective spot in the visual field chart of the target person 4. In a possible embodiment, the local feature data further comprises distance data indicating a distance of the respective spot to a visual field defect border in a visual field chart of the target person 4. The local feature data can further comprise a visual field position of the respective spot in the visual field chart of the target person. In a possible embodiment, the local feature data further comprises a residual function value of a spot in a visual field chart of the target person 4.

FIG. 1 shows an embodiment wherein a visual sensory organ 3 of a target person 4 is treated by applying a visual stimulation signal. In another embodiment, the apparatus 1 is provided for stimulating an auditory sensory organ 3 of the target person 4, i.e. an ear of the target person 4. In this embodiment, the stimulation signal is an acoustic signal wherein the treatment parameters of the acoustical signal are adjusted by the processing unit 9.

In a further embodiment, the sensory organ 3 of the target person 4 is a touch organ of the person which is stimulated by a vibration signal. This vibration signal is generated by a stimulation device 2 formed by a vibrator.

The storage device 10 as shown in FIG. 1 can be formed by a remote data base connected to the processing unit 9 of the apparatus 1 via a network. In a possible embodiment, the processing unit 9 has access to the storage device 10 via a server which is connected to the processing unit 9 via a network, such as the internet. In an alternative embodiment, the storage device 10 is a local memory integrated within the apparatus 1. In the storage device 10, sensory data of a reference group of persons is stored. This reference group of persons can comprise a plurality of other patients or persons which have been treated by the same treatment as the target person 4. By using a treatment outcome prediction model (TOPM), the treatment parameters of the used treatment are optimized by executing a data mining algorithm in the processing unit 9. Features which are associated with the treatment outcome are derived from the pre-stimulation diagnostic charge. By using a data pool of a reference group having the same sensory defect as the target person 4 it is possible to predict areas in the sensory field topography where restoration or recovery is most likely to occur. This allows a prediction of the treatment outcome and also to optimize the treatment for the respective target person 4. Each target person 4 is treated individually on the basis of calculated recovery prediction data output by a data mining algorithm on the basis of measured sensory data of the target person 4 and on the basis of stored sensory data of a reference group of persons already treated by the same treatment.

Figure 2:
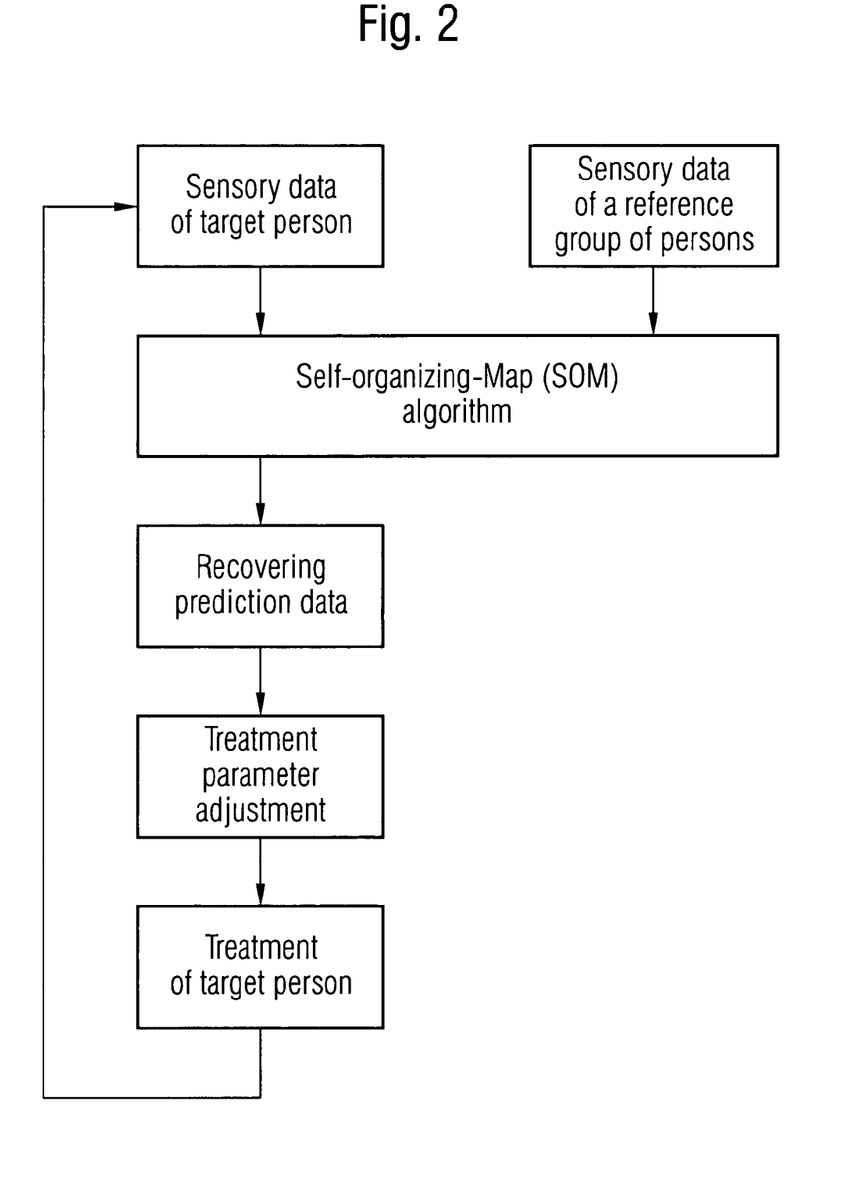
FIG. 2 shows a flowchart of a possible embodiment of a method for automatic adjustment of a treatment for a target person according to the present invention.

FIG. 2 shows a simple flowchart for illustrating a method for automatic adjustment of a treatment according to a possible embodiment of the present invention. The sensory data of a target person 4 measured by the detection device 5 as well as the sensory data of a reference group of persons treated by the same treatment and stored in the sensory device 10 are input to the processing unit 9. The processing unit 9 executes a self-organizing map algorithm to calculate recovery prediction data predicting a change of a sensory function of said target person 4 in response to the treatment. On the basis of the calculated recovery prediction data, the processing unit 9 forms a treatment parameter adjustment and controls the stimulation device 2 accordingly. The stimulation device 2 generates the stimulation signal having treatment parameters as adjusted by the adjustment unit 9. Then, the sensory data of the target person 4 is detected again, for example after a predetermined time period.

Being able to predict treatment outcome using pretreatment variables is important to optimize therapy of a patient. To achieve a prediction of a treatment outcome, methods of machine learning can be combined with a priori information data of a specific disease to be able to forecast specific treatment effects. The ability to predict a treatment outcome is not only useful to gain further insight into mechanisms of plasticity, i.e. contributing factors to recovery, but it aids the clinician to estimate efficacy in an individual patient or target person 4 and can provide hints at improving efficacy. A prediction model in the field of visual system plasticity is provided using Self-Organizing-Maps (SOM) as the core of a treatment outcome prediction model (TOPM). The SOM is an algorithm which offers excellent data visualization and can also be used for classification and prediction. The SOM is applied to data obtained from patients or target persons 4 with visual field defects caused e.g. by brain damage due to stroke, brain trauma or other etiologies. Such visual field defects can be improved by systematically presenting visual stimuli at the border region of the damaged visual field using Vision Stimulation Training (VST). Because normally neither all patients nor all areas of the visual field profit from the treatment, it is desirable to provide a method that efficiently predicts vision restoration. The methods of outcome prediction employed by the present invention have also a general value in its applicability to other medical problems where topographic diagnostic charts are used. The method and apparatus according to the present invention uses a TOPM which allows the prediction of the extent and topographic distribution of recovery of visual functions in individual patients.

The visual system information pathway begins at the retina where light is transformed to electrophysiological signals which are transmitted by the retinal ganglion cells through the optic nerve to other brain regions. The primary and most important stream of information travels through the thalamus, where information is relayed onto geniculate neurons which, in turn, send their axons directly to the primary visual cortex located in the occipital lobe. The primary visual cortex (also called "V1") computes basic features of visual images and scenes and works in concert with many "higher" brain regions with which it is reciprocally connected. The visual system is the largest sensory processing system in the brain of a person. About 30-50% of the cerebral cortex is committed to process visual information which compares to only 8% in the auditory and 7% in the somatosensory system. This is the reason why brain damage due to stroke or head injury is often accompanied by loss of visual functions as expressed by partial or total blindness. The loss of visual function as well as its restoration (recovery) can be assessed by behavioral tests, where the target person 4 is asked to respond to small target stimuli presented in a random fashion to the visual field of the target person 4. Depending on the performance of the patient or target person (responding or not responding to the stimulus by pressing a button), diagnostic charts are obtained which describe the location of areas of relative or total blindness as shown in FIG. 3.

Figure 3A:
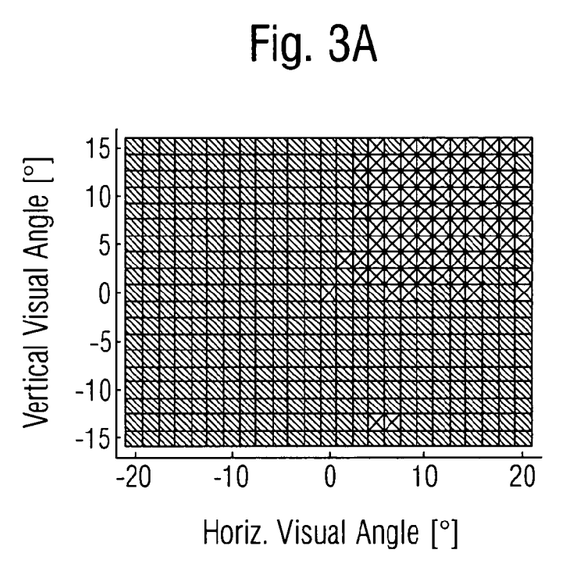
FIGS. 3A, 3B show examples for visual field diagnostic charts as employed in a possible embodiment of the apparatus according to the present invention.
Figure 3B:
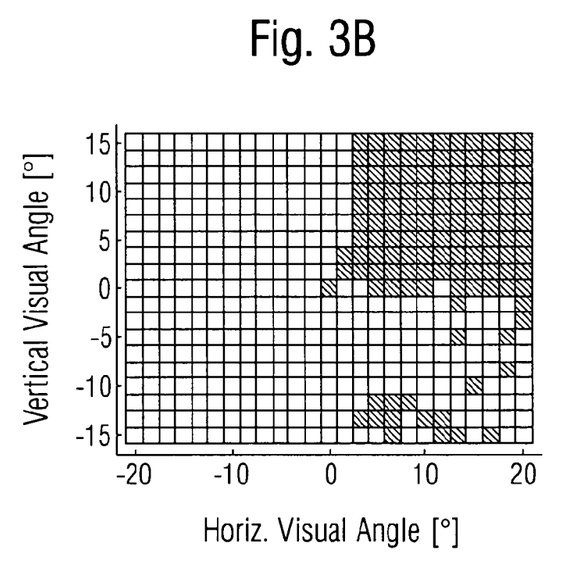

FIGS. 3A, 3B show visual field diagnostic charts obtained from computer-based visual field assessments. In each respective location of the chart, three above-threshold stimuli are presented at random time intervals and locations.

FIG. 3A shows reaction time charts (averaged among three test stimuli per position). A minimal response time is coded in white ($\approx$377 ms), a maximal response time is coded in black ($\approx$888 ms). Detection misses (without any responses) are represented by a cross. A tendency is apparent that the perception of stimuli is slower in intact areas of the bottom right hemi-field than in the intact areas of the left hemi-field.

FIG. 3B shows detection chart areas with either complete blindness in black (0 out of 3 stimuli were acknowledged by the subject; chart value: 0), or intact vision in white (3/3 acknowledged test stimuli; chart value: 1) or areas of residual vision in gray (1/3 or 2/3 stimulus presentations were acknowledged, chart value: 1/3, 2/3). The chart of FIG. 3B is a chart of a target person suffering from a quadrantanopia, indicating a minor and distributed deficit in the lower right quadrant and a total loss in the upper right quadrant. The diagnostics chart resolution is GX=25×GY=19 stimuli (background luminance: 86 cd/m$^2$, stimulus luminance: 23 cd/m$^2$, stimulus size: 0.4°, inter-stimulus distance: 1.7°). To reduce eye movements that can compromise treatment efficacy, the target person 4 fixates in a possible embodiment on a central fixation point and responds to color changes (catch trials) presented at random intervals.

Diagnostic visual field charts VFC as shown in FIGS. 3A, 3B are an important part of neurological and ophthalmologic examination. Visual field diagnostic testing detects and localizes defective areas and monitors dynamic changes (deterioration or recovery) of the visual field of a target person 4. The size, form and location of a given visual field defect (also called scotoma) are indicative of where the damage may specifically be located in the visual pathway. One static diagnostic test is the High Resolution Perimetry (HRP), which assesses the visual field in high spatial resolution with bright, high-contrast (super-threshold) stimuli. The visual stimuli are presented on a computer screen 2 which is positioned at e.g. 40 cm in front of the target person 4 while the head of the target person 4 is stabilized with a chin rest to reduce body and head movements during a diagnostic session. The target person 4 can respond by pressing a button 7 whenever the presented test stimuli are perceived. During the diagnostic procedure, the target person 4 fixates on a static point at the centre of the diagnostic area, i.e. the fixation spot. The diagnostic output is a topographic chart for each target person 4 which schematically illustrates the visual field defect. Several single diagnostic tests—which are assessed shortly after each other—are superimposed to obtain a chart that displays visual detections (MapDetection) and reaction times (MapReactionTime). This computer-based perimetric procedure examines the central visual field (±20°) and its validity and reliability were established elsewhere. On the basis of the detection charts, three different types of spots can be defined depending on their state of functionality (intact vision, total defect or residual vision). These three diagnostic spot types are defined by the concept of a stencil:

$$\text{stencil}_{Defect}(x, y) = \begin{cases} 1 & \text{iff } \text{map}_{Detection}^{Baseline}(x, y) = 0 \\ 0 & \text{else} \end{cases} \quad (1)$$

$$\text{stencil}_{Intact}(x, y) = \begin{cases} 1 & \text{iff } \text{map}_{Detection}^{Baseline}(x, y) = 1 \\ 0 & \text{else} \end{cases} \quad (2)$$

$$\text{stencil}_{Residual}(x, y) = \begin{cases} 1 & \text{iff } \text{map}_{Detection}^{Baseline}(x, y) = \frac{1}{3} \cup \frac{2}{3} \\ 0 & \text{else} \end{cases} \quad (3)$$

The greatest plasticity of the visual system can be found during the postnatal state but can also be seen in adulthood in the short phase of weeks or months after visual system damage. A Vision Stimulation Training (VST) is applied to target persons or patients 4 with a visual field damage. The principle of VST is to visually stimulate the visual field border in order to repetitively activate partially damaged regions located between areas of the intact and defective visual field. The treatment area is adjusted regularly depending on the progress of the respective patient. For example when hemianopic patients carry out a visual stimulation treatment one hour per day for a period of six months, significant improvements (enlargements) of the visual field can be observed. The method and apparatus according to the present invention is provided to predict a recovery and is based on an outcome prediction model with which the extent and location of visual field recovery and restoration can be estimated.

Medical prognosis is the prediction of a future course and outcome of disease processes, which may either concern their natural course or their outcome after treatment. In contrast to predicting the type of a disease, treatment outcome prediction considers a time component. In general, a treatment outcome prediction model TOPM can be used as a tool to select the treatment with the highest expected benefit to the target person 4. The prediction model TOPM extends the knowledge of the physician by the data base of the model and can offer the benefit of a second opinion. The TOPM used by the method and apparatus according to the present invention predicts the outcome of intrasubject visual field areas. The local prediction is "spot-based", wherein a spot is a point in the visual field. The treatment outcome of a specific spot is either improvement, i.e. the spot is a "hot spot" or no improvement, i.e. the spot is a "cold spot".

Figure 4:
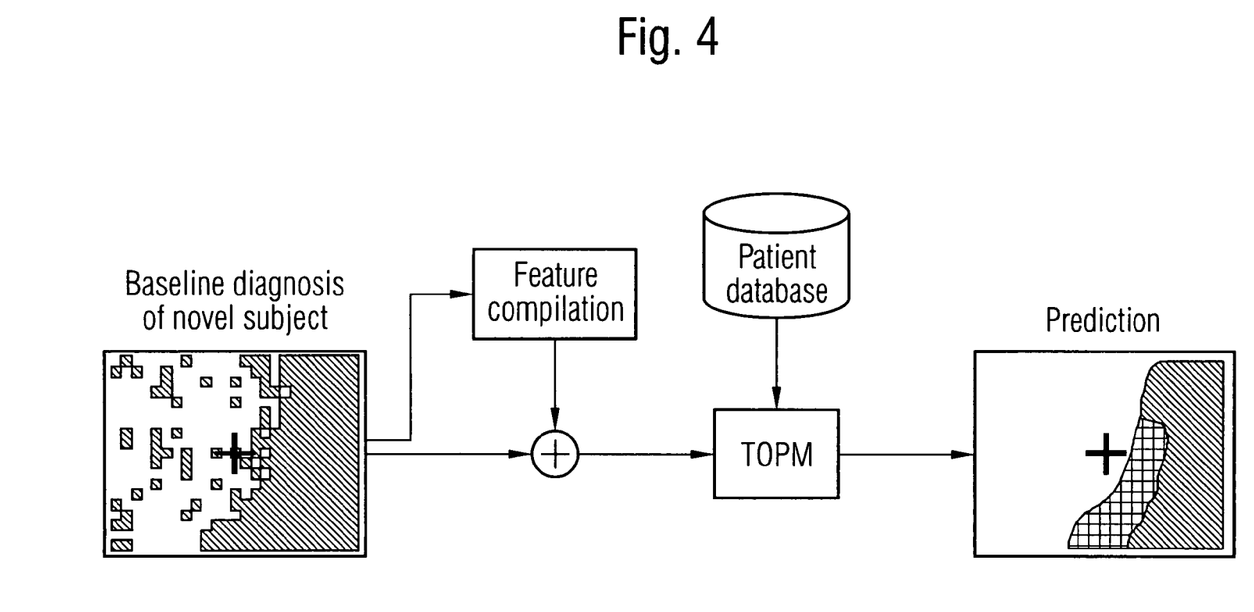
FIG. 4 shows a flowchart for prediction of a treatment outcome according to a possible embodiment of the present invention.

The TOPM methodology is comprised by the following three steps as shown in FIG. 4. In a first step, a treatment outcome prediction model TOPM is provided which can predict a treatment outcome based on the baseline diagnosis by using diagnostic charts from a reference group of patients who completed a Vision Stimulation Training VST. In a second step predetermined features are extracted from baseline diagnostic charts. In these baseline performance charts, the spots are classified as being either "impaired" (e.g. spots with 0 or 1 out of 3 possible detections) or "intact" (spots with 2 or 3 out of 3 detections). Based on the extracted features from the second step treatment outcome for all impaired spots by using the TOPM derived the first step is predicted in a third step.

A supervised database is provided to support a self organizing map (SOM) learning and cross validation which contains pairs of baseline and post-treatment diagnostic charts from a number of selected patients. Charts from another group of patients (not part of the learning or test set) can be used as examples to compare the actual with the predicted outcome charts.

FIG. 4 shows a flow chart for prediction of a treatment outcome according to a possible embodiment of the present invention. The baseline diagnostics (left) assesses the visual field of a target person 4 before visual stimulation training VST (the cross represents the center of vision). From the diagnostic chart, feature data is extracted directly or computed incorporating a priori information data stored in database. The TOPM calculates a predicted treatment outcome of impaired spots based on the data stored in a patient database storing sensory data of a reference group. The prediction chart shows areas of likely improvements (hatching) or lack of improvement (black area) after vision stimulation training VST.

Feature selection is the task of deciding what feature data is relevant with respect to the target classification, i.e. treatment outcome. The suitability of feature which is used for the TOPM can determine the performance of the treatment outcome prediction model TOPM more than the choice of an classification algorithm.

Features are selected which can be extracted from diagnostic reaction time and detection charts (such as shown in FIGS. 3A, 3B). The feature data is grouped into global and local feature data. Global feature data address chart related information data while local features relate to a specific spot in a visual chart of a person.

Global feature data comprise the size of the residual and defect area, a reaction time, conformity and border diffuseness.

The defective sector of a visual field of a target person 4 is usually rather compact and covers large areas of the visual field, i.e., up to half of the visual field in patients with hemianopia and about a quarter in quadrantanopia (as shown in FIG. 5).

Figure 5A:
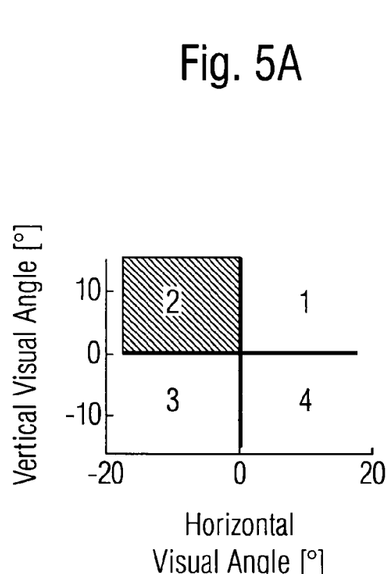
FIGS. 5A, 5B, 5C show prototypic visual field effects as used as a basis for feature data as employed by the apparatus and method according to the present invention.
Figure 5B:
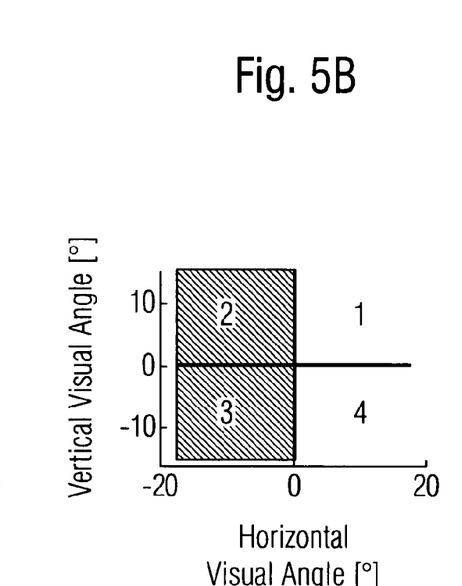
Figure 5C:
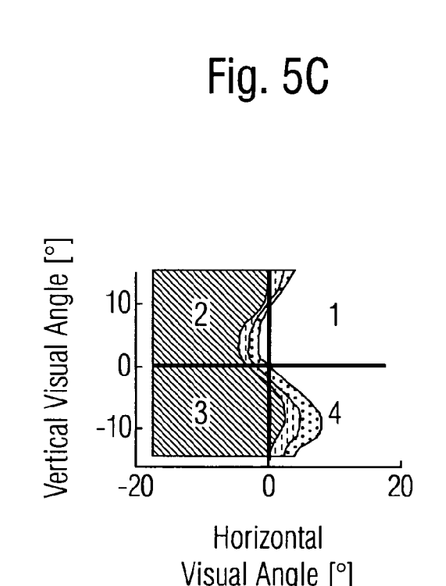

Areas of residual vision are usually located at or near the border region that separates the seeing field from the blind region. But residual vision can also occur in $$\text{Defect Area} = \sum_{y=1}^{GY} \sum_{x=1}^{GX} \text{stencil}_{Defect}(x, y) \quad (4)$$

$$\text{Residual Area} = \sum_{y=1}^{GY} \sum_{x=1}^{GX} \text{stencil}_{Residual}(x, y) \quad (5)$$

compact areas within the defect or intact visual field. Both features are included in the treatment outcome prediction model TOPM and are computed in a possible embodiment as follows:

FIGS. 5A, 5B, 5C show prototypic visual field defects. Homonymous quadrantanopia (left) in the upper left quadrant and hemianopia (middle) of the left hemifield. Many patients have a border zone which is not as sharp as in FIG. 5A and FIG. 5B but shows variable performance, i.e., broken up with residual spots forming a diffuse residual border as shown in FIG. 5C.

The reaction time can vary largely between and within subjects or patients. The reaction time is considered in the treatment outcome prediction model TOPM and computed only from intact spots.

$$\text{Reaction Time} = \frac{\sum_{y=1}^{GY} \sum_{x=1}^{GX} (\text{Map}_{Reaction\ Time}^{Baseline}(x, y) \cdot \text{stencil}_{Intact}(x, y))}{\sum_{y=1}^{GY} \sum_{x=1}^{GX} \text{stencil}_{Intact}(x, y)} \quad (6)$$

The Conformity to hemianopia and quadrantanopia expresses the degree of similarity of the visual field of the target person 4 with an "ideal" hemianopia and quadrantanopia as shown in FIGS. 5A, 5B. The exact hemianopia (i.e. one hemifield completely intact and the other hemifield completely blind, as shown in FIG. 5B, is rare. It is usually caused by total anatomical damage of the visual system in one hemisphere or results from a complete cut of the optic radiation. Both features are considered in the treatment outcome prediction model TOPM because the clinical experience indicates that a restoration is unlikely if a visual field defect is complete and close to the ideal form. These features are based on combined values from the ratio of defect spots (ratioidefect) and the homogeneity of the i-th quadrant (noisei):

$$\text{degree}_{defect}^i = \text{ratio}_{defect}^i \cdot (1 - \text{noise}^i) \quad (7)$$

The conformity to hemianopia and quadrantanopia is calculated in a possible embodiment by combining the degreedefect values from all four quadrants such that, e.g., quadrantanopia of the second quadrant is represented by many defect spots in the second quadrant with little noise and many intact spots with little noise in the first, third and fourth quadrant:

$$Hemianopia = \max\left\{\begin{array}{l} \text{degree}_{defect}^1 \cdot \text{degree}_{defect}^4 \cdot (1 - \text{degree}_{defect}^2) \cdot (1 - \text{degree}_{defect}^3) \\ \text{degree}_{defect}^2 \cdot \text{degree}_{defect}^3 \cdot (1 - \text{degree}_{defect}^1) \cdot (1 - \text{degree}_{defect}^4) \end{array}\right\} \quad (8)$$

$$Quadrantanopia = \max\left\{\begin{array}{l} \text{degree}_{defect}^1 \cdot (1 - \text{degree}_{defect}^2) \cdot \\ (1 - \text{degree}_{defect}^3) \cdot (1 - \text{degree}_{defect}^4) \\ \text{degree}_{defect}^2 \cdot (1 - \text{degree}_{defect}^1) \cdot \\ (1 - \text{degree}_{defect}^3) \cdot (1 - \text{degree}_{defect}^4) \\ \text{degree}_{defect}^3 \cdot (1 - \text{degree}_{defect}^2) \cdot \\ (1 - \text{degree}_{defect}^1) \cdot (1 - \text{degree}_{defect}^4) \\ \text{degree}_{defect}^4 \cdot (1 - \text{degree}_{defect}^2) \cdot \\ (1 - \text{degree}_{defect}^3) \cdot (1 - \text{degree}_{defect}^1) \end{array}\right\} \quad (9)$$

Border Diffuseness, i.e. the extent to which the visual field border is diffuse or sharp, is an important parameter which is also typically related to the size of residual vision. A diffuseness measure is computed by calculating a ratio of residual spots among all spots in the border area. The border area is for example 5° wide and located between the defect and intact area as shown in FIG. 6. The border is defined as 'diffuse' if many residual spots lay inside the border area and 'sharp' if almost no residual spots are inside the visual scotoma border.

In order to predict a treatment outcome for each spot, local feature data and therefore spot-related features are introduced extending the global feature data. The local feature data can comprise a distance to scotoma, a visual field position, neighborhood measures and a residual function.

The distance between a spot and the visual fields defect border, i.e. scotoma border (see e.g. FIG. 6B), can be estimated in cortical coordinates. By using a coordinate transformation model visual field coordinates are transformed in a possible embodiment into cortical coordinates considering the cortical magnification factor. The distance to scotoma feature is considered in the treatment outcome prediction model TOPM because the distance to the scotoma, i.e. visual field defect border, is significantly (negatively) correlated with its restoration, i.e., restoration of vision is greatest in spots close to the visual field border.

Figure 6A:
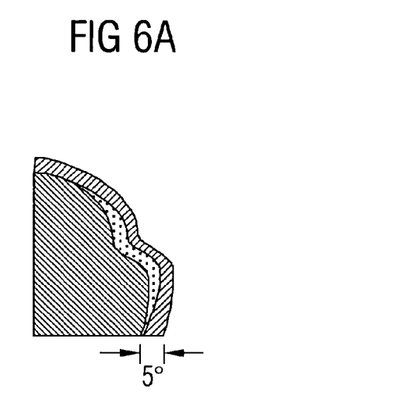
FIGS. 6A, 6B illustrate two border-related features as employed by a possible embodiment of the apparatus and method according to the present invention.
Figure 6B:
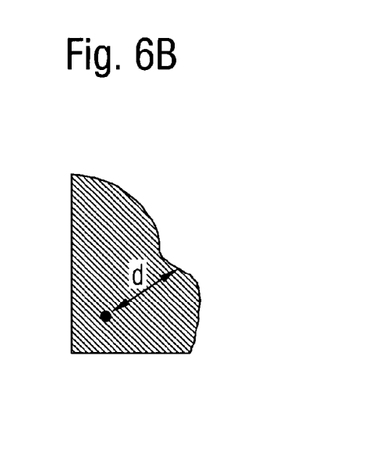

FIGS. 6A, 6B show two border related features. FIG. 6A shows a global feature Border Diffuseness which measures the fraction of residual spots within the border area (hatching) which is defined as the area which touches the defect area and extends 5° into the residual (gray) or intact area (white). FIG. 6B shows as a local feature Distance to Scotoma which measures the distance (d) between a spot and the defect border and is estimated in cortical coordinates considering cortical magnification.

Figure 7:
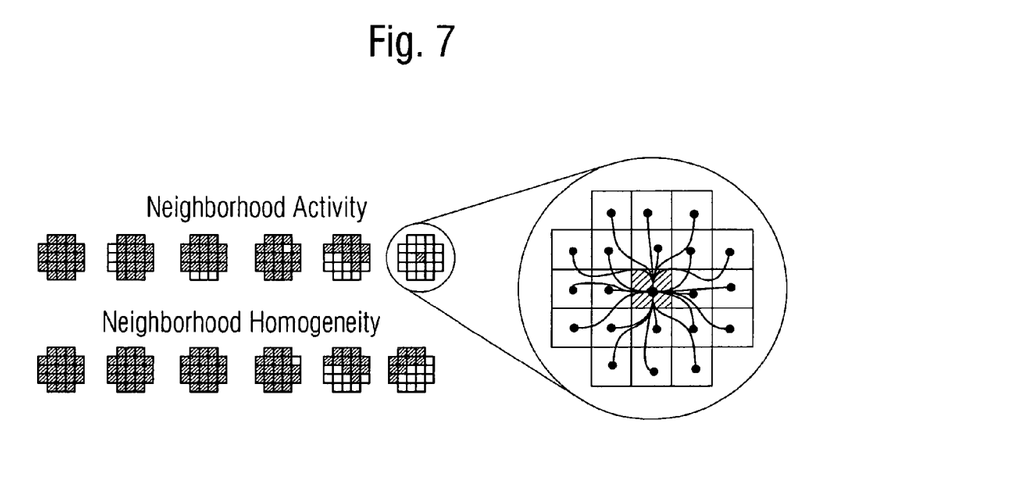
FIG. 7 illustrates different examples of neighborhood data as employed as feature data by the apparatus and method according to the present invention.

Hot and cold spots are not uniformly distributed in the visual field but are a function of the location of the visual scotoma and therefore the visual field position is considered in the TOPM. The vertical eccentricity is positively correlated with the amount of the defect border shift The probability of restoration is associated with the average activity of spots within a 5° visual angle around a damaged spot as illustrated by FIG. 7. If the surrounding is more intact and therefore physiologically more active, restoration is more likely. The Neighborhood Activity around restored spots is significantly higher than around spots not showing restoration. Lateral horizontal connections in the visual cortex explain such a center-surround relationship between neurons in the primary visual cortex (see FIG. 7 right). Another measure to describe the neighborhood is the variability of the residual activity in the immediate surrounding of the respective spot which is the standard deviation of the average Neighborhood Activity.

FIG. 7 shows a schematic illustration representing examples of different neighborhoods that are differentiated into Neighborhood Activity (top row) and Neighborhood Homogeneity (bottom row). They are ordered from low to high activity and from high to low homogeneity. The activity and the homogeneity is based on the concept of the local spatial neighborhood which is inspired by the connectivity between neurons (shown in cartoon on the right) where intrinsic horizontal connections (indicated by branches) exist between neurons.

In contrast to Border Diffuseness which measures the amount of Residual Function of the whole border, the residual function is directly related to the respective spot itself and measures the strength of damage to a spot (0 or 1 of 3 detected stimuli; spots with 2 or 3 detections are not considered because they are not classified as impaired). It represents as the probability of stimulus detection at the specific spot position. A significantly higher Residual Function of restored spots can be found in comparison to non-restored spots. This dichotomous feature has a high predictive weight. The Residual Function of each spot is equal to the detection chart value at the respective position (x, y):

$$\text{Residual Function}(x, y) = \begin{cases} 0 & \text{iff } \text{map}_{Detection}^{Baseline}(x, y) = 0 \\ \frac{1}{3} & \text{iff } \text{map}_{Detection}^{Baseline}(x, y) = \frac{1}{3} \end{cases} \quad (10)$$

The provision of a treatment outcome prediction model TOPM requires selecting an appropriate classification algorithm. Self-organizing maps (SOMS), are based on relatively simple mathematical operations. The most complex operation in SOM learning is the calculation of the Euclidean distance in multidimensional space. Self-organizing maps can be used for correlation hunting, unsupervised and supervised cluster analysis, multivariate feature analysis as well as for novelty detection and classification.

Self-organizing maps (SOM) reduce the number of dimensions from the feature space spanned by the features to low dimensions. The SOM surface is usually two-dimensional and consists of map units that enable the data to be visualized while preserving the topography of the original feature space. Each map unit represents a specific position in the feature space and becomes a highly sensitive feature detector during the learning process. After supervised learning, novel data samples are classified by using k-nearest neighbor (k-NN) classification with parameter k equal to 1. The classification depends on the label of the SOM unit with smallest Euclidian distance to the novel sample.

Figure 8:
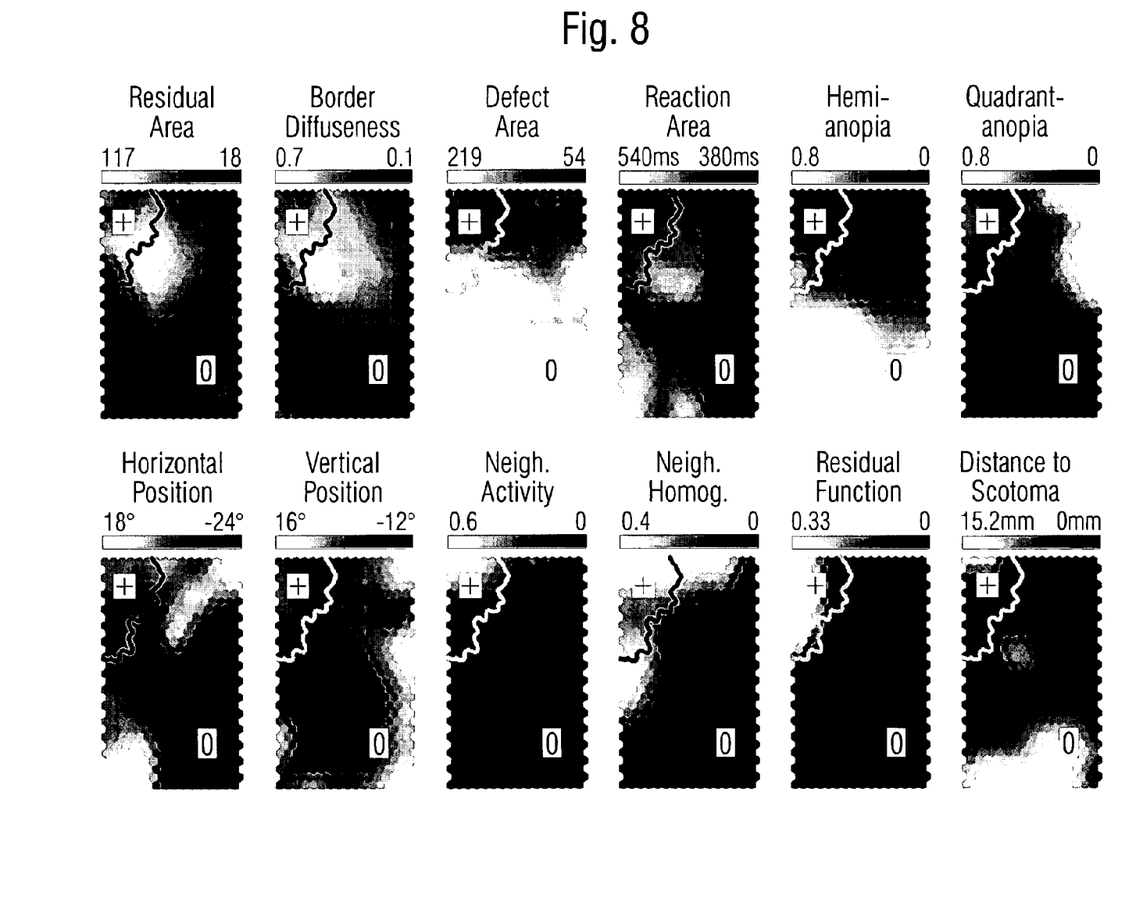
FIG. 8 shows different component plains of global and local feature data extracted by baseline diagnostic data in a possible embodiment of the apparatus and method according to the present invention.

SOM-based data exploration can be carried out on two dimensional component planes (such as shown in FIG. 8).

These planes exist for each feature and are compromised of the map units (the horizontal and vertical axis of the component planes have no specific name or meaningful interpretation). These planes are feature-specific projections onto the SOM surface after learning is finished. Each map unit represents a specific point in the n-dimensional feature space (where n is the number of features). Due to the cooperative concept in SOM learning, adjacent map units have similar feature values. The component planes and map units are shown for 12 features in FIG. 8. Each map unit always has the same position in each of the 12 component planes. Map units are labeled as hot ('+') and cold spots ('0'). The label is not shown for each map unit because the map is separated compactly between hot and cold spot map units. Each data sample in the learning data base is assigned to exactly one map unit (minimizing the distance between map unit and data sample). The topography of hot and cold spots in the component planes after learning is relatively robust if the learning process is repeated.

The distance between the closest cold and hot spot map units in Euclidian space is relatively broad in comparison to the distance between map units belonging to the same class (this can be concluded from a distance matrix). This shows that there is a 'natural' difference between cold and hot spots in the sample distribution. Further, a robust discrimination between cold and hot spots in prediction is possible.

FIG. 8 shows component planes of global (top row) and local (bottom row) features extracted from the baseline diagnostic. The distribution of values of the respective feature is shown for hot ('+') and cold ('0') spots.

By evaluation of the component planes as shown in FIG. 8a a relationship between a treatment outcome and the various features as well as interdependencies is determined. For example high values in the size of the Residual Area are associated with hot spots whereas most cold spots are not (low values of this feature in the cold spot region). The example of FIG. 8 shows a more pronounced separation between hot and cold spots in contrast to Reaction Time where the component chart appears more uniform in gray. Almost no restoration (cold spots) can be determined in charts with small Residual Area (black color). A univariate model with Hemianopia or Reaction Time alone is not appropriate as a separator between hot and cold spots. Residual Area and Border Diffuseness are strongly positively correlated. Hemianopia and Quadrantanopia are strongly negatively correlated considering the color distribution of the respective features in the component planes.

The following six component planes belong to local features (see FIG. 8 bottom row). The Residual Function is the best discriminator between hot and cold spots; only few map units in the hot spot region have a low value of Residual Function. All map units which are labeled 'hot spot' represent data samples which have a Neighborhood Activity and Neighborhood Homogeneity well above zero (white and gray color). A univariate model with Horizontal or Vertical Position alone is not appropriate to discriminate between cold and hot spots because map units of both classes represent data samples of middle values (gray). Most data samples with high distance to the visual field defect border, i.e. scotoma border, border (white color) are cold spots but not all hot spots are located near the scotoma border (black color). The features Neighborhood Homogeneity and Neighborhood Activity are strongly correlated (the color formation looks familiar in both component planes).

In general, the shown component charts indicate that global feature data of the visual charts as a whole are less appropriate for classification than local feature data. The colors in the local feature data (FIG. 8 bottom row) show a better association with the map unit labeling of hot and cold spots in comparison to the color distribution of the global feature data (FIG. 8 top row).

Figure 9:
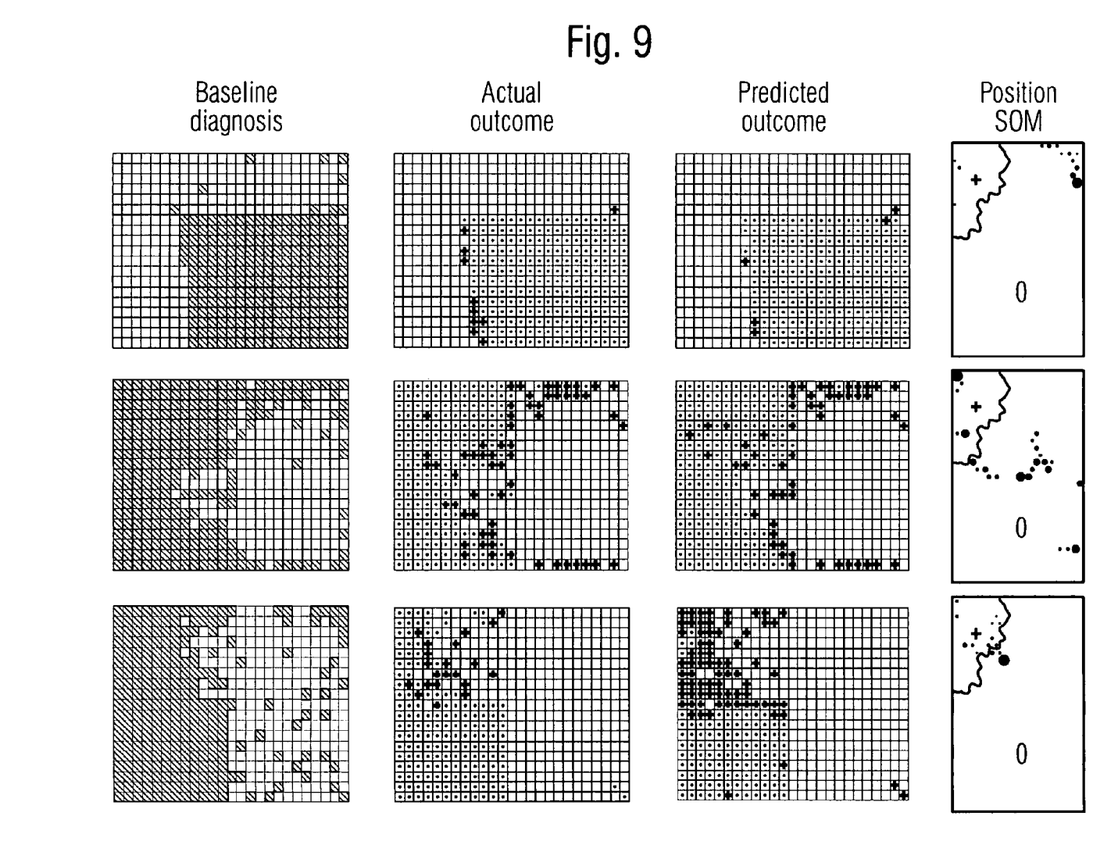
FIG. 9 shows diagnostic charts of different patients for illustrating a possible embodiment of the apparatus and method according to the present invention.

In order to compare the prediction outcome with the actual treatment outcome, predicted results are shown in FIG. 9. Feature data is extracted from baseline charts of three patients (see FIG. 9, left column) and then predicted with the treatment outcome prediction model TOPM.

The patients are selected randomly before the treatment outcome prediction model TOPM is constructed. The respective charts are not part of SOM learning.

The predicted charts are obtained by using the developed treatment outcome prediction model TOPM according to the schema shown in FIG. 3. Values of the global and local feature data are initially extracted for each spot such that the location of each spot in the 12 dimensional feature space is located. Secondly, by using the k-NN algorithm with k=1 the best matching SOM unit is determined for each spot which determines thereafter the predicted class (hot or cold) of the respective spot. The actual as well as the predicted treatment outcome is shown in FIG. 9 (second and third column). The actual treatment outcome is computed in a possible embodiment as follows:

$$\text{Actual outcome}(x, y) = \begin{cases} \text{'hot spot'} & \text{iff } \text{map}^{Baseline}_{Detection}(x, y) <= \frac{1}{3} \cap \\ & \text{map}^{Post}_{Detection}(x, y) >= \frac{2}{3} \\ \text{'cold spot'} & \text{iff } \text{map}^{Baseline}_{Detection}(x, y) <= \frac{1}{3} \cap \\ & \text{map}^{Post}_{Detection}(x, y) <= \frac{1}{3} \end{cases} \quad (11)$$

In order to locate the best matching SOM unit for all spots of each individual chart, the projection of all samples in the diagnostic chart onto the SOM surface is shown in FIG. 9 (right column). Almost all samples of the first chart (FIG. 9, top row) are located at the top right position in the SOM. According to the component planes, this area is more strongly related to Quadrantanopia, with small Residual Area and low Residual Function. Spots of the second diagnostic chart (FIG. 9, middle row) are spread widely on the SOM, the top left corner is related to maximal Neighborhood Activity and the aggregation in the map center is related to negative horizontal coordinates covering positive and negative vertical coordinates with low Neighborhood Activity which describes the defective hemifield on the left. In the third diagnostic chart, the strongest aggregation of spots is located closely to the hot spot border within the region of cold spots (FIG. 9, bottom row). This region is related to negative vertical coordinates with a similarity to both, quadrantanopia and hemianopia with sharp borders. These spots belong to the lower left part of the semi-quadrantanopic diagnostic chart which has also many defects in the upper quadrant of the left hemifield.

FIG. 9 shows diagnostic charts of three patients which are not part of the learning or verification data set (first column). The actual treatment outcome is shown in the second column (hot '+' or cold '.' spot). The third column shows the predicted treatment outcome for each impaired spot at baseline. The location of spots from individual baseline charts projected onto the SOM is shown in the right column. The respective SOM location differs widely among the three patients (higher frequencies are indicated by a larger circle size) and reflects the respective values of global and local features.

A k-fold-cross validation can be selected to evaluate the performance of the treatment outcome prediction model TOPM. Cross validation is a resampling method where the test data set is first divided into k disjunctive sets. Instead of calculating only one evaluation measure, k-fold-cross validation offers a more robust evaluation. Therefore, the performance measurement procedure is repeated k times using k−1 sets ($\lambda$) for SOM learning and the remaining set ($\Gamma$) is used as test data set. The patient database 10 can therefore be used for learning and evaluation as well. As a result, the average among all k evaluation measurements is reported. In comparison to other methods, cross validation is an unbiased and robust estimation of the generalization error but with higher standard deviation of the obtained measures. With 10-fold cross validation, 10 classifiers are trained and then evaluated with the test samples. Standard evaluation measures can be used to calculate an average True-Positive-Rate (TPR=44%±4.7%, how many hot spots were classified correctly) and a False-Positive-Rate (FPR=6%±1.9%, how many cold spots were classified as hot spots) among all 10 classifiers according to:

$$TPR = \frac{TP}{P} \quad (12)$$

$$FPR = \frac{FP}{N} \quad (13)$$

which is based on the number of positive (P, hot spots) and negative samples (N, cold spots) in Γ, as well as the number of correctly classified positive samples (TP) and incorrectly classified negative samples (FP). The average accuracy (ACC=84.2%±1.4%) measures the amount of correctly classified samples and is in the given example slightly better than the average baseline accuracy (ACCbaseline=81%±1.3%) which is the ratio of samples labeled with the most frequent class. Both measures are computed as follows (the former uses the number of correctly classified negative samples, TN):

$$ACC = \frac{TP + TN}{P + N} \quad (14)$$

$$ACC_{baseline} = \frac{\max(P, N)}{P + N} \quad (15)$$

The small difference between accuracy and baseline accuracy is a result of the strong skewness of the class distribution because the learning database contained in the given example 7026 cold spots but only 1689 hot spots.

A measure which is robust to skewed class distributions is the receiver operating characteristic (ROC) and can therefore used as a standard procedure in performance evaluation of classifiers in the medical domain. All trained classifiers are located close to each other in the ROC space represented by the value of their respective TPR and FPR as shown in FIG. 10A.

Figure 10A:
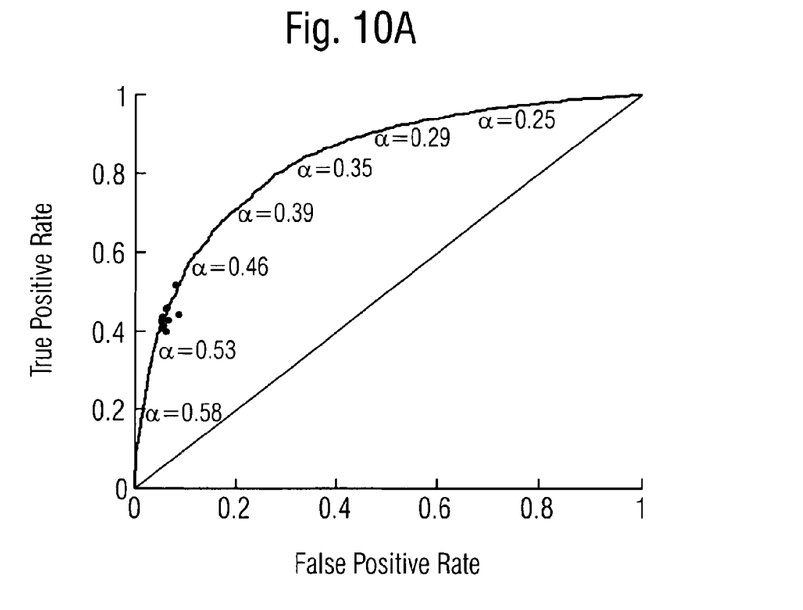
FIGS. 10A, 10B show diagrams for illustrating receiver operating characteristics according to a possible embodiment of the method and apparatus according to the present invention.
Figure 10B:
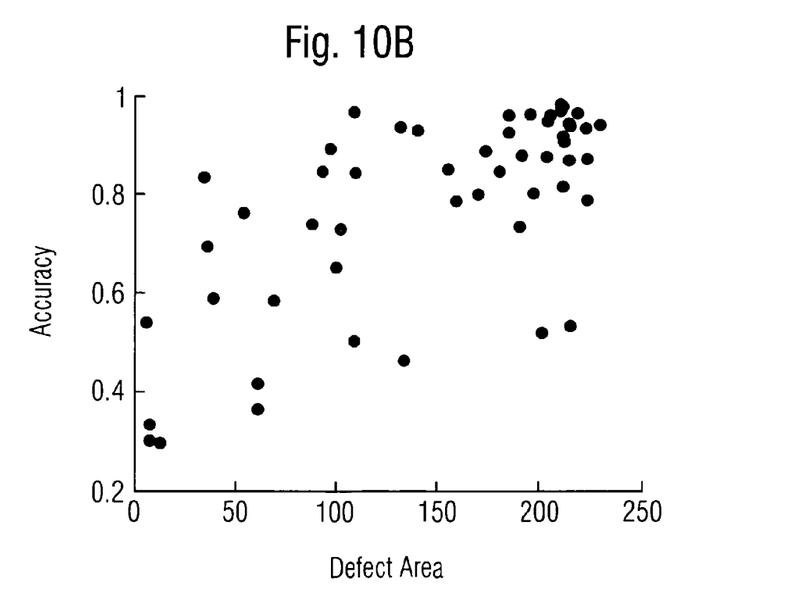

FIG. 10A shows a receiver operating characteristic (ROC) for the TOPM in prognosis of hot and cold spots in 10-fold cross-validation (single points). The continuous ROC-curve is calculated by using 1-nearest neighbor classification considering different thresholds a (see text). FIG. 10B shows in comparison to 10-fold cross validation where the database was divided into 10 parts, the spots in the database were divided into N=52 parts with respect to patient affiliation. The prediction accuracy was determined for all individual charts in leave-one-out cross validation and were plotted against the feature Defect Area. Diagnostic charts with a large defect area have higher prognostic accuracy than charts with only few defect areas.

A more robust performance measure is achieved if a continuous ROC curve and the area under the ROC curve (AUC=0.81) is computed for the classifier instead of just a single point in the ROC space. The curve is obtained by using an increasing threshold a (ranging from $-\infty$ to $+\infty$) and a score which is interpreted as probability that the sample belongs to the predicted class. For each discrete value of α, all samples (i in Γ) are labeled with respect to their score and α as follows:

$$\text{label}_i = \begin{cases} \text{'hot spot'} & \text{iff } \alpha \geq \text{score}_i \\ \text{'cold spot'} & \text{iff } \alpha < \text{score}_i \end{cases} \quad (16)$$

and the respective rate of correctly labeled positive samples (TPR) and incorrectly labeled negative samples (FPR) determine points in the ROC space which form a continuous curve (see FIG. 10A left). For computation of the score a simple measure is used which is based on the distance between the sample and the nearest map unit with positive (dhot) and negative class (dcold). The score of the i-th sample is the relative distance:

$$\text{score}_i = \frac{d_{cold}}{d_{hot} + d_{cold}} \quad (17)$$

which is a value between '0' (indicating that the i-th sample is close to a map unit labeled 'cold spot' and distant to the next 'hot spot' map unit) and '1' (close to 'hot spot' and distant to 'cold spot').

The appropriateness of the treatment outcome prediction model TOPM to several subclasses of patients is of relevance. By separating the samples with respect to patient affiliation, leave-one-out cross validation shows that the performance is not equal for each target person 4 resulting in a high range of individual performance measures (minimal accuracy=29%, maximal accuracy=98%). A strong correlation between accuracy and the feature Defect Area (ρ=0.67) indicates (see FIG. 10B right) that the accuracy of diagnostic charts with many defect areas is better than in charts with only few defect areas.

The SOM forms the core of the prediction model. Its nonlinearity and self-organization methodology allows a comprehensible adaptation to the data distribution. Although other prediction models may perform comparably well, SOMs simplify the process of data mining and the feature selection phase as they conveniently combine both, prediction and data exploration.

The employed treatment outcome prediction model TOPM allows prediction of restoration of vision and plasticity of impaired or blind topographic areas in the visual field of patients with visual system damage. The treatment outcome prediction model TOPM includes features that are associated with the treatment outcome as assessed by reference groups. The features incorporate a priori information data and address several topics in the broad field of vision plasticity.

The invention claimed is:

1. An apparatus for automatic adjustment of a treatment of a target person to be treated based on calculated recovery prediction data for predicting a change of a sensory function of said target person in response to said treatment, which comprises:
    a stimulation device, the stimulation device generating a stimulation signal applied to a sensory organ of the target person;
    at least one detection device, the at least one detection device measuring sensory data of the target person in response to the stimulation signal applied to the sensory organ of the target person;
    a processing unit, the processing unit receiving the sensory data measured by the at least one detection device; and
    a storage device, the storage device storing the sensory data of the target person and sensory data of a reference group of other persons already treated with the stimulation signal;
    wherein the stimulation signal generated by the stimulation device includes treatment parameters;
    wherein the processing unit calculates recovery prediction data, and automatically adjusts at least one of the treatment parameters of the stimulation signal generated by the stimulation device based on the calculated recovery prediction data, the recovery prediction data predicting a change of a sensory function of the target person in response to the treatment applied to the target person;
wherein the recovery prediction data calculated by the processing unit is based on sensory data of the target person measured by the at least one detection device stored in the storage device and is based on the sensory data of the reference group of other persons stored in the storage device;
wherein the processing unit uses a self-organizing map (SOM) algorithm in calculating the recovery prediction data to automatically adjust the at least one of the treatment parameters of the stimulation signal generated by the stimulation device and applied to the sensory organ of the target person;
wherein said sensory data comprises global feature data and local feature data;
wherein said local feature data comprises neighborhood data of a spot in a visual field chart of said target person; and
wherein the global feature data comprises conformity data of a visual field chart of said target person indicating a degree of similarity of the visual field to heminopia and quadrantanopia.

2. An apparatus for automatic adjustment of a treatment of a target person to be treated based on calculated recovery prediction data for predicting a change of a sensory function of said target person in response to said treatment, which comprises:
　a stimulation device, the stimulation device generating a stimulation signal applied to a sensory organ of the target person;
　at least one detection device, the at least one detection device measuring sensory data of the target person in response to the stimulation signal applied to the sensory organ of the target person;
　a processing unit, the processing unit receiving the sensory data measured by the at least one detection device; and
　a storage device, the storage device storing the sensory data of the target person and sensory data of a reference group of other persons already treated with the stimulation signal;
　wherein the stimulation signal generated by the stimulation device includes treatment parameters;
　wherein the processing unit calculates recovery prediction data, and automatically adjusts at least one of the treatment parameters of the stimulation signal generated by the stimulation device based on the calculated recovery prediction data, the recovery prediction data predicting a change of a sensory function of the target person in response to the treatment applied to the target person;
　wherein the recovery prediction data calculated by the processing unit is based on sensory data of the target person measured by the at least one detection device stored in the storage device and is based on the sensory data of the reference group of other persons stored in the storage device;
　wherein the processing unit uses a self-organizing map (SOM) algorithm in calculating the recovery prediction data to automatically adjust the at least one of the treatment parameters of the stimulation signal generated by the stimulation device and applied to the sensory organ of the target person;
　wherein said sensory data comprises global feature data and local feature data;
　wherein said local feature data comprises distance data indicating a distance of a spot in a visual field chart of said target person to a visual field defect border; and
　wherein the global feature data comprises conformity data of a visual field chart of said target person indicating a degree of similarity of the visual field to heminopia and quadrantanopia.

* * * * *